(12) United States Patent
Legatt

(10) Patent No.: US 8,506,077 B2
(45) Date of Patent: Aug. 13, 2013

(54) METHOD FOR MEASURING VISUAL FUNCTION AND VISUAL ATTENTION IN A CONTINUOUS PERFORMANCE TEST

(75) Inventor: Michael E. Legatt, Austin, TX (US)

(73) Assignee: Computer Psych, LLC, Austin, TX (US)

( * ) Notice: Subject to any disclaimer, the term of this patent is extended or adjusted under 35 U.S.C. 154(b) by 588 days.

(21) Appl. No.: 12/806,707

(22) Filed: Aug. 19, 2010

(65) Prior Publication Data

US 2011/0063572 A1    Mar. 17, 2011

Related U.S. Application Data

(63) Continuation of application No. 11/881,175, filed on Jul. 26, 2007, now abandoned.

(60) Provisional application No. 60/834,502, filed on Jul. 31, 2006.

(51) Int. Cl.
*A61B 3/00* (2006.01)

(52) U.S. Cl.
USPC .......................................... 351/200; 351/246

(58) Field of Classification Search
USPC .......................................... 351/200–203, 246
See application file for complete search history.

(56) References Cited

U.S. PATENT DOCUMENTS

| | | | | |
|---|---|---|---|---|
| 4,146,311 | A | * | 3/1979 | Murr .............................. 351/226 |
| 4,586,796 | A | * | 5/1986 | Molteno ....................... 351/206 |
| 4,953,968 | A | * | 9/1990 | Sherwin et al. ............... 351/211 |
| 2002/0103429 | A1 | | 8/2002 | deCharms |
| 2004/0023952 | A1 | | 2/2004 | Leventhal |

* cited by examiner

*Primary Examiner* — James Greece
(74) *Attorney, Agent, or Firm* — Robert S. Stoll; Richard P. Silverman

(57) ABSTRACT

The invention comprises a neuropsychological test method designed to measure a test subject's variables of visual attention for stimuli believed to preferentially elicit specific visual pathways. Target visual pathways include the magnocellular on/off, parvocellular chromatic red/green, koniocellular blue/yellow, and parvocellular achromatic pathways. Furthermore, the invention computes differential measures between the different stimuli types for diagnostic value. These computations include, but are not limited to, measures believed to elicit non-linear contrast gain control, on versus off pathways, and changes in performance over time. The test displays both target and noise (non-target) stimuli with different apriori probabilities at different stages of the test. The test can capture and analyze physiological measures, isoluminant points and critical flicker fusion points. In accordance with the present invention, a novel method and system called the "Variable Contrast Continuous Performance Test (VC-CPT)" is provided.

15 Claims, 3 Drawing Sheets

FIG 2

| ABBREVIATION | FULL NAME | CONTRAST | COLOR | BACKGROUND |
|---|---|---|---|---|
| $M_{ON}$ | MAGNOCELLULAR ON | + 6% | LIGHT GRAY | GRAY |
| $M_{OFF}$ | MAGNOCELLULAR OFF | - 6% | DARK GRAY | GRAY |
| $PC_G$ | PARVOCELLULAR CHROMATIC GREEN | 0% | GREEN | GRAY |
| $PC_R$ | PARVOCELLULAR CHROMATIC RED | 0% | RED | GRAY |
| $KN_B$ | KONIOCELLULAR BLUE | 0% | BLUE | GRAY |
| $KN_Y$ | KONIOCELLULAR YELLOW | 0% | YELLOW | GRAY |
| $PN_{UP}$ | PARVOCELLULAR ACHROMATIC ON-UP | MODULATES +48% ± 16% INITIAL UPWARD | GRAY | GRAY |
| $PN_{DN}$ | PARVOCELLULAR ACHROMATIC ON - DOWN | MODULATES +48% ± 16% INITIAL DOWNWARD | GRAY | GRAY |
| $PF_{UP}$ | PARVOCELLULAR ACHROMATIC OFF-UP | MODULATES -48% ± 16% INITIAL UPWARD | GRAY | GRAY |
| $PF_{DN}$ | PARVOCELLULAR ACHROMATIC OFF-DOWN | MODULATES -48% ± 16% INITIAL DOWNWARD | GRAY | GRAY |
| $CG_{ON}$ | NON-LINEAR CONTRAST GAIN CONTROL ON | + 50% | WHITE | GRAY |
| $CG_{OFF}$ | NON-LINEAR CONTRAST GAIN CONTROL OFF | - 50% | BLACK | GRAY |

| # | ISI | p | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| 1 | 2 | 50 | $PF_{UP}$ | $KN_Y$ | $PF_{DN}$ | $KN_Y$ | $PF_{DN}$ | $KN_B$ | $PC_R$ | $CG_O$ | $PN_{UP}$ | $KN_B$ | $PC_G$ | $M_{ON}$ | $CG_{OF}$ | $CG_O$ | $PN_D$ | $PN_D$ |
| 2 | 1 | 50 | $PN_D$ | $CG_O$ | $PC_R$ | $PC_G$ | $PN_D$ | $KN_B$ | $M_{ON}$ | $KN_Y$ | $M_{OFF}$ | $KN_Y$ | $PF_{UP}$ | $PN_{UP}$ | $CG_{OF}$ | $M_{ON}$ | $M_{OFF}$ | $PF_{UP}$ |
| 3 | 4 | 50 | $M_{OFF}$ | $PC_R$ | $KN_Y$ | $PC_R$ | $CG_{OF}$ | $M_{ON}$ | $PF_{UP}$ | $PN_D$ | $PC_G$ | $CG_{OF}$ | $CG_O$ | $PF_{UP}$ | $KN_B$ | $PF_{DN}$ | $PN_{UP}$ | $PC_G$ |
| 4 | 1 | 25 | $M_{ON}$ | $PF_{UP}$ | $PF_{UP}$ | $M_{ON}$ | $PN_D$ | $PC_R$ | $PF_{DN}$ | $M_{OFF}$ | $CG_{OF}$ | $CG_O$ | $M_{OFF}$ | $M_{ON}$ | $PC_G$ | $PC_G$ | $PN_D$ | $CG_O$ |
| 5 | 2 | 25 | $PC_G$ | $PF_{UP}$ | $PF_{UP}$ | $PN_{UP}$ | $M_{OFF}$ | $KN_B$ | $PC_G$ | $PC_R$ | $PN_{UP}$ | $KN_Y$ | $CG_O$ | $PC_R$ | $PF_{DN}$ | $PN_{UP}$ | $M_{OFF}$ | $PN_D$ |
| 6 | 4 | 25 | $M_{ON}$ | $KN_Y$ | $PF_{DN}$ | $M_{OFF}$ | $PF_{UP}$ | $PN_D$ | $PN_D$ | $CG_O$ | $PC_R$ | $M_{OFF}$ | $PF_{UP}$ | $PN_D$ | $PC_R$ | $CG_{OF}$ | $PN_D$ | $PF_{DN}$ |
| 7 | 2 | 75 | $PF_{DN}$ | $CG_O$ | $KN_Y$ | $M_{ON}$ | $PF_{UP}$ | $M_{ON}$ | $PN_{UP}$ | $CG_{OF}$ | $PN_{UP}$ | $CG_O$ | $PN_{UP}$ | $PC_R$ | $PC_R$ | $M_{ON}$ | $PF_{DN}$ | $CG_O$ |
| 8 | 4 | 75 | $M_{OFF}$ | $PN_D$ | $M_{ON}$ | $PN_{UP}$ | $PC_R$ | $PC_G$ | $PC_R$ | $M_{OFF}$ | $PC_R$ | $PF_{DN}$ | $CG_O$ | $PC_R$ | $PC_G$ | $PN_D$ | $CG_O$ | $KN_Y$ |
| 9 | 1 | 75 | $PF_{DN}$ | $PN_{UP}$ | $KN_Y$ | $KN_B$ | $PN_D$ | $M_{OFF}$ | $CG_O$ | $M_{OFF}$ | $PN_{UP}$ | $M_{OFF}$ | $PC_R$ | $M_{OFF}$ | $PF_{DN}$ | $KN_Y$ | $PF_{UP}$ | $PC_G$ |
| 10 | 2 | 50 | $M_{OFF}$ | $M_{ON}$ | $CG_{OF}$ | $PN_D$ | $M_{OFF}$ | $PC_G$ | $PC_R$ | $KN_Y$ | $PC_R$ | $M_{OFF}$ | $CG_{OF}$ | $KN_B$ | $PN_D$ | $KN_Y$ | $M_{ON}$ | $PC_R$ |
| 11 | 1 | 50 | $PC_G$ | $KN_Y$ | $CG_{OF}$ | $PC_R$ | $M_{OFF}$ | $PC_G$ | $CG_O$ | $CG_O$ | $PC_R$ | $CG_{OF}$ | $KN_B$ | $M_{OFF}$ | $PN_D$ | $KN_B$ | $M_{ON}$ | $PN_{UP}$ |
| 12 | 4 | 50 | $PC_G$ | $CG_O$ | $PN_{UP}$ | $PC_R$ | $PF_{UP}$ | $KN_B$ | $KN_B$ | $PC_R$ | $PF_{UP}$ | $KN_B$ | $PF_{DN}$ | $M_{ON}$ | $PF_{UP}$ | $M_{ON}$ | $M_{OFF}$ | $PF_{DN}$ |
| 13 | 1 | 25 | $PC_G$ | $PN_D$ | $PN_{UP}$ | $PC_G$ | $PF_{UP}$ | $PC_R$ | $PF_{DN}$ | $PN_D$ | $CG_{OF}$ | $KN_Y$ | $CG_O$ | $PF_{UP}$ | $CG_O$ | $M_{ON}$ | $CG_O$ | $PC_G$ |
| 14 | 2 | 25 | $PF_{UP}$ | $KN_B$ | $M_{OFF}$ | $M_{ON}$ | $CG_O$ | $PN_{UP}$ | $PF_{UP}$ | $KN_Y$ | $PF_{DN}$ | $KN_Y$ | $PC_R$ | $KN_B$ | $PN_D$ | $KN_B$ | $PF_{DN}$ | $CG_{OF}$ |
| 15 | 4 | 25 | $PC_R$ | $PC_G$ | $CG_O$ | $PN_{UP}$ | $M_{ON}$ | $M_{OFF}$ | $KN_Y$ | $PN_D$ | $CG_O$ | $M_{OFF}$ | $PF_{UP}$ | $PF_{UP}$ | $PN_D$ | $M_{ON}$ | $CG_O$ | $CG_{OF}$ |
| 16 | 2 | 25 | $PC_R$ | $CG_{OF}$ | $PN_{UP}$ | $PF_{UP}$ | $KN_Y$ | $CG_{OF}$ | $KN_Y$ | $KN_Y$ | $PC_R$ | $KN_Y$ | $PN_{UP}$ | $PF_{UP}$ | $PC_G$ | $-PF_{UP}$ | $M_{OFF}$ | $CG_{OF}$ |
| 17 | 4 | 75 | $PC_G$ | $PC_G$ | $M_{OFF}$ | $PN_{UP}$ | $PF_{DN}$ | $KN_Y$ | $PN_{UP}$ | $M_{ON}$ | $PF_{UP}$ | $M_{OFF}$ | $M_{ON}$ | $PF_{DN}$ | $PF_{DN}$ | $M_{ON}$ | $PN_{UP}$ | $PC_G$ |
| 18 | 1 | 75 | $PF_{UP}$ | $PF_{UP}$ | $PF_{DN}$ | $PN_{UP}$ | $PN_{UP}$ | $KN_B$ | $KN_Y$ | $PF_{DN}$ | $CG_{OF}$ | $M_{OFF}$ | $PN_{UP}$ | $CG_O$ | $CG_O$ | $-PF_{UP}$ | $M_{OFF}$ | $KN_B$ |
| 19 | 2 | 75 | $PC_R$ | $CG_O$ | $CG_O$ | $CG_{OF}$ | $M_{OFF}$ | $M_{OFF}$ | $KN_B$ | $PF_{UP}$ | $CG_O$ | $CG_{OF}$ | $M_{ON}$ | $PN_D$ | $M_{OFF}$ | $M_{ON}$ | $PN_D$ | $M_{ON}$ |
| 20 | 1 | 50 | $PC_R$ | $PF_{DN}$ | $PF_{DN}$ | $KN_Y$ | $PN_{UP}$ | $KN_Y$ | $PN_D$ | $PN_D$ | $PF_{DN}$ | $PN_D$ | $M_{ON}$ | $PN_D$ | $PN_{UP}$ | $M_{OFF}$ | $PN_{UP}$ | $PN_{UP}$ |
| 21 | 4 | 50 | $PC_G$ | $PC_G$ | $CG_O$ | $PF_{DN}$ | $PC_G$ | $PC_G$ | $PC_G$ | $PC_G$ | $PC_G$ | $CG_O$ | $PN_{UP}$ | $CG_O$ | $CG_O$ | $PC_R$ | $PN_D$ | $PN_{UP}$ |
| 22 | 1 | 25 | $PF_{UP}$ | $PF_{UP}$ | $PC_G$ | $M_{ON}$ | $M_{OFF}$ | $KN_Y$ | $M_{ON}$ | $M_{OFF}$ | $KN_B$ | $KN_B$ | $M_{ON}$ | $KN_Y$ | $PN_D$ | $KN_Y$ | $KN_B$ | $PC_R$ |
| 23 | 2 | 25 | $PF_{DN}$ | $M_{OFF}$ | $M_{OFF}$ | $KN_Y$ | $PN_{UP}$ | $KN_B$ | $PC_G$ | $PC_G$ | $KN_Y$ | $CG_O$ | $PC_G$ | $PN_D$ | $PN_D$ | $M_{OFF}$ | $PF_{DN}$ | $M_{OFF}$ |
| 24 | 4 | 25 | $PF_{DN}$ | $PC_G$ | $PC_G$ | $KN_Y$ | $PC_G$ | $KN_Y$ | $CG_O$ | $PC_R$ | $KN_Y$ | $PN_D$ | $CG_{OF}$ | $PN_D$ | $PN_D$ | $M_{ON}$ | $PC_R$ | $M_{OFF}$ |
| 25 | 2 | 75 | $KN_Y$ | $PC_G$ | $M_{OFF}$ | $CG_O$ | $CG_{OF}$ | $KN_B$ | $PN_{UP}$ | $PC_G$ | $PC_R$ | $PC_G$ | $PF_{DN}$ | $KN_Y$ | $PF_{UP}$ | $CG_{OF}$ | $PC_R$ | $CG_{OF}$ |
| 26 | 4 | 75 | $KN_B$ | $KN_B$ | $KN_B$ | $CG_O$ | $PF_{UP}$ | $KN_B$ | $KN_Y$ | $M_{ON}$ | $PC_R$ | $CG_O$ | $KN_Y$ | $PN_D$ | $PF_{DN}$ | $M_{ON}$ | $PF_{DN}$ | $CG_{OF}$ |
| 27 | 1 | 75 | $CG_{OF}$ | $KN_B$ | $CG_O$ | $KN_B$ | $PN_D$ | $PC_R$ | $PC_G$ | $PF_{UP}$ | $PN_D$ | $PC_R$ | $CG_{OF}$ | $M_{ON}$ | $M_{OFF}$ | $KN_Y$ | $PF_{UP}$ | $PN_{UP}$ |

FIG 3

METHOD FOR MEASURING VISUAL FUNCTION AND VISUAL ATTENTION IN A CONTINUOUS PERFORMANCE TEST

CROSS-REFERENCE TO RELATED APPLICATIONS

Reference is made to provisional patent application 60/834,502, filed Jul. 31, 2006, to which claim of priority is hereby made pursuant to 35 U.S.C. 120, and U.S. application Ser. No. 11/881,175, filed Jul. 26, 2007 now abandoned, which is hereby incorporated by reference.

TECHNICAL FIELD OF THE INVENTION

This invention relates to the field of computer-based testing and neuropsychological/neuroscientific testing.

BACKGROUND OF THE INVENTION

In 1956, Rosvold, Mirsky, Sarason, Bransom and Beck, developed the first continuous performance test (CPT), a task of visual attention that measured an individual's ability to sustain performance over time, termed vigilance. Since that original CPT, several variants of the test have been developed, often with good reliability in distinguishing individuals without neurological impairment from those with attention deficit/hyperactivity disorder, schizophrenia, traumatic brain injury, dementia, Parkinson's disease, and developmental dyslexia, to name a few (Riccio, C. A., Reynolds, C. R., Lowe, P. A. (2001). Clinical applications of continuous performance tests: Measuring attention and impulsive responding in children and adults. New York: Wiley).

Many continuous performance tests function through the visual medium, displaying stimuli to which participants are instructed to respond or ignore based on some salient features of the stimuli. For example, in the Conners' Continuous Performance Test (Conners, C. K. (2000). Conners' Continuous Performance Test (CPT-II): Computer program for Windows, technical guide and software manual. Multi-Health Systems New York), a stimuli that should not receive a response (noise stimuli) is a single letter 'X' on the screen, while all other single letters on the screen should receive a response (target stimuli). Another popular CPT, the Cornblatt Identical-Pairs CPT (Cornblatt, B. A., & Kelip, J. G. (1994). Impaired attention genetics, and the patho-physiology of schizophrenia. Schizophrenia Bulletin, 20 (1), 31-46) assigns target stimuli to a number or image that repeats twice.

From the results of several trials, CPT tasks are used to measure several components of executive function. Executive function includes the sustaining of attention, maintaining of response sets, set-shifting, problem solving, and planning and following through on tasks (Cohen, R. A. (1993). Attentional control: Subcortical and frontal lobe influences. In R. A. Cohen (Ed.), The neuropsychology of attention (pp. 219-254). New York: Plenum Press).

While neuropsychological models of executive function and attention contain areas throughout the brain, the majority of the components are contained in the frontal lobe and its projections. Individuals with focal frontal lobe damage most often complain of difficulties in attention and concentration (Riccio, C. A., Reynolds, C. R., Lowe, P. A. (2001). Clinical applications of continuous performance tests: Measuring attention and impulsive responding in children and adults. New York: Wiley).

Visual CPT tasks tend to rely on stimuli that, based on current understanding of the visual system, intrinsically trigger several visual pathways. However, deficits in a participant's visual system would likely reduce CPT task performance, indicating that the task is in fact not fully measuring visual attention, but visual function as well.

For example, presume a stimulus presentation on a typical CPT task. When a CPT stimulus spontaneously appears on the screen, the hard boundaries between the character's edge and background and sudden large-scale changes in luminance in the regions of the character are likely to trigger a magnocellular response in an individual with intact magnocellular function. The magnocellular response is faster than the response of other cells. Therefore, on average, an individual with deficient magnocellular function will perceive the appearance of the character more slowly and therefore will respond later. However, the individual's attention may still be strong, but inaccurately measured as deficient.

Visual dysfunction is noted in many disorders. Magnocellular-pathway deficits are noted to occur in developmental dyslexia (Omtzigt, D., Hendriks, A. W., & Kolk, H. H. J. (2002). Evidence for magnocellular involvement in the identification of flanked letters. Neuropsychologia, 40, 1881-1890). NMDA-based non-linear contrast gain control (Zemon, V., Butler, P. D., Gordon, J., Jalbrzikowski, M., Javitt, D. C., Piesco, J., Russo, J., & Schechter, I. (2004). Neural dysfunction in schizophrenia: contrast-response functions and a nonlinear model, Program No. 347.122004 Abstract Viewer and Itinerary Planner. Washington, D.C. Society for Neuroscience, Online; Butler, P. D., Zemon, V., Schechter, I., Saperstein, A. M., Hoptman, M. J., Lim, K. O., Revheim, N., Silipo, G., & Javitt, D. C. (2005). Early-Stage Visual Processing and Cortical Amplification Deficits in Schizophrenia. Archives of General Psychiatry, 62 (5), 495-504; Kwon, Y. H., Nelson, S. B., Toth, L. J., & Sur, M. (1992). Effect of stimulus contrast and size on NMDA receptor activity in cat lateral geniculate nucleus. Journal of Neurophysiology, 68, 182-195) and magnocellular deficits (Butler, P. D., Zemon, V., Schechter, I., Saperstein, A. M., Hoptman, M. J., Lim, K. O., Revheim, N., Silipo, G., & Javitt, D. C. (2005). Early-Stage Visual Processing and Cortical Amplification Deficits in Schizophrenia. Archives of General Psychiatry, 62 (5), 495-504; Schechter, I., Butler, P. D., Silipo, G., Zemon, V., & Javitt, D. C. (2003). Magnocellular and parvocellular contributions to backward masking dysfunction in schizophrenia. Schizophrenia Research, 64, 91-101) are found in schizophrenia. Magnocellular, parvocellular, and koniocellular deficits are found in Parkinson's disease (Silva, M. F., Faria, P., Regaterio, F. S., Forjaz, V., Januario, Freire, A., Castelo-Branco, M. (2005). Independent patterns of damage within magno-, parvo- and koniocellular pathways in Parkinson's disease. Brain, 128 (10), 2260-2271). In traumatic brain injury, magnocellular deficits are noted in children with extremely low birth weights (Downie, A. L., Jakobson, L. S., Frisk, V., Ushycky, I. (2003). Periventricular brain injury, visual motion processing, and reading and spelling abilities in children who were extremely low birthweight. Journal of the International Neuropsychological Society, 9 (3), 440-449), and cortical gain control deficits are noted in adults (Du, T., Ciuffreda, K. J., Kapoor, N. (2005). Elevated dark adaptation thresholds in traumatic brain injury. Brain Injury, 19 (13), 1125-1138).

Therefore, this invention was developed, based on the current understanding of the visual system, to provide a novel method to assess visual attention in each visual pathway discretely. The invention aims to provide a more accurate representation of the contributive roles of visual function and visual attention in a participant's performance.

BRIEF SUMMARY OF THE INVENTION

In accordance with the present invention, a novel method and system called the "Variable Contrast Continuous Performance Test (VC-CPT)" is provided for simultaneously measuring a participant's visual attention and visual pathway functioning in a non-invasive neuropsychological test setting.

This system is designed to measure visual attention and executive function. This system is unique in its ability to administer stimuli designed to preferentially elicit each visual pathway separately, therefore providing a far more detailed picture into the degree of function in the visual system, separating out deficits in the input and attentional areas. Furthermore, this system is unique in its ability to compare and contrast function between specific visual pathways, able to build a profile of visual function that may further help differentiate between conditions.

This system is non-invasive. Many approaches to measuring visual function involve the use of visual evoked potential (VEP) studies or magnetic resonance imaging (MRI) studies to assess function. Other non-invasive means of measuring visual attention and visual function (e.g., Cheng, A., Eysel, U. T., Vidyasagar, T. R. (2004). The role of the magnocellular pathway in serial deployment of visual attention. European Journal of Neuroscience, 20 (8), 2188-2192; Omtzigt, D., Hendriks, A. W., & Kolk, H. H. J. (2002). Evidence for magnocellular involvement in the identification of flanked letters. Neuropsychologia, 40, 1881-1890) focus on a particular visual pathway (most often one of the magnocellular pathways). By overcoming these limitations, this system is able to offer higher accuracy in reporting visual attention, and to better offer clinical and research utility in the diagnosis and investigations of conditions that affect visual attention and/or the visual system.

This invention is able to measure a participant's response in a continuous fashion (rather than a discrete up/down fashion). Therefore, it is able to provide measures of "near fires," in which the participant begins to press but inhibits the response before completion. This invention can be configured to measure response in either a press-down or press-up fashion, which can lead to a further differential measure and greater sense of executive control, as the button-up paradigm tends to be more cognitively taxing (Cornblatt, B. A., & Kelip, J. G. (1994). Impaired attention, genetics, and the patho-physiology of schizophrenia. Schizophrenia Bulletin, 20 (1), 31-46)

This invention is able to receive data from several different physiological measurement devices, including, but not limited to, galvanic skin response, heart rate, and blood pressure devices. Therefore, this invention is able to provide a more accurate measurement of the participant's physiological arousal, yielding additional data as to the degree of difficulty a participant has in completing the task.

This invention is further able to receive data from an eye tracking system. Therefore, it is able to determine whether a stimulus is viewed properly. It also may have utility in determining whether ocular difficulties (such as macular degeneration and focal brain injury) are present.

As the underlying assumptions for signal detection theory (SDT) are not always met during a testing session, the invention additionally computes non-linear detection theory measures (Macmillan, N. A., Creelman, C. D. (1991). Detection theory: a user's guide. New York: Cambridge University Press) to provide more mathematically appropriate and accurate measures.

Because different monitors and video card combinations tend to display the same gray levels with different luminance levels, this invention is designed to link with a photometer to determine the exact luminance levels that occur for each possible color value on the screen. Therefore, the presentation of stimuli should be nearly identical from one system to another. The instrument is further able to present stimuli of two or more levels per check, and therefore able to approximate a mean luminance with far greater accuracy than uniform checks of a near value.

Due to the nature of the task, this instrument collects measurements of critical flicker fusion and points of isoluminance for red/green and blue/yellow.

The system uses a standard personal computer system with attached monitor. The computer system is expected to have a video card capable of displaying images at a high (32 and 64-bit) color depth, high refresh rate (120 Hz or higher), and high resolution. At present, the ability to achieve sufficient luminance brightness and reliability is largely limited to cathode-ray tube (CRT) displays. Depending on the intended mode of administration (binary or continuous), either an attached mouse or custom switch is connected as well.

The system's operation entails a test participant taking a brief (under twenty-minute) test, during which he or she is instructed to press or release a lever (mouse button or custom switch) in response to the presentation of an array of squares. Participants are instructed not to respond to an array of circles. The invention has three different a priori probability levels (25%, 50% and 75% that a stimulus is a target), allowing for differential measures of performance between probabilities.

Stimuli believed to preferentially elicit the magnocellular pathway are presented with a spontaneous onset, at a low percentage above ($M_{ON}$) or below ($M_{OFF}$) the background gray luminance level. Currently, the invention has been tested with values 8% and 6%. Stimuli believed to preferentially elicit the parvocellular chromatic pathways are presented at isoluminance, as red ($PC_R$) or green ($PC_G$) stimuli against a gray background. Stimuli believed to preferentially elicit the koniocellular pathway are presented at isoluminance, as blue ($KN_B$) or yellow ($KN_R$) stimuli against a gray background. Stimuli believed to preferentially elicit the parvocellular achromatic-on pathway modulate around a high positive background contrast (pedestal), starting at background, ramping to the pedestal, and then modulating first downward ($PN_{DN}$) or upward ($PN_{UP}$). Stimuli believed to preferentially elicit the parvocellular achromatic-off pathway modulate around a high negative background contrast (pedestal), starting at background, ramping to the pedestal, and then modulating first downward ($PF_{DN}$) or upward ($PF_{UP}$). In order to assess the functioning of the NMDA-based non-linear contrast gain control system, stimuli are presented with a spontaneous onset at a high percentage (50%) above ($CG_{ON}$) and below ($CG_{OFF}$) the background luminance level. See FIG. 2 for further information on these stimulus types.

Each stimulus is designed to focally target an individual visual pathway, including the magnocellular on ($M_{ON}$), magnocellular off ($M_{OFF}$), parvocellular chromatic red ($PC_R$), parvocellular chromatic green ($PC_G$), koniocellular blue ($KN_B$), koniocellular yellow ($KN_Y$), parvocellular achromatic on ($PN_{UP}$ and $PN_{DN}$), parvocellular achromatic off ($PF_{UP}$ and $PF_{ON}$), and non-linear contrast gain control-modulated on ($CG_{ON}$) and off ($CG_{OFF}$) stimuli. See FIG. 2 for further information on these stimuli.

Upon completion of the test session, the system computes performance variables utilizing techniques including signal detection theory (SDT), choice theory (CT), non-parametric detection theory (NPDT), and response time measures. These variables are computed for each group of stimuli individually, for groups of stimuli, and for differentials between stimuli and groups, for each a priori probability, and across all probabilities.

It is believed that this method can be used to develop ranges of performance in a normal population, as well as for particular conditions, including, but not limited to, schizophrenia (active, remissive, and close blood relative), ADHD, dementia, Parkinson's disease, developmental dyslexia, and traumatic brain injury.

BRIEF DESCRIPTION OF THE DRAWING

FIG. 2 shows the twelve types of stimuli currently used in the invention.

FIG. 3 shows the presentation pattern for the stimuli in the invention. In order to address concerns that certain population are unable to complete an entire test, the bulk of the data is computed within the first nine blocks (equaling approximately six minutes twelve seconds), although the whole test contains three such groupings totaling approximately eighteen minutes, thirty-six seconds. Underlined stimuli correspond to target stimuli, while non-underlined stimuli correspond to noise stimuli.

DETAILED DESCRIPTION OF THE INVENTION

Figure 1:
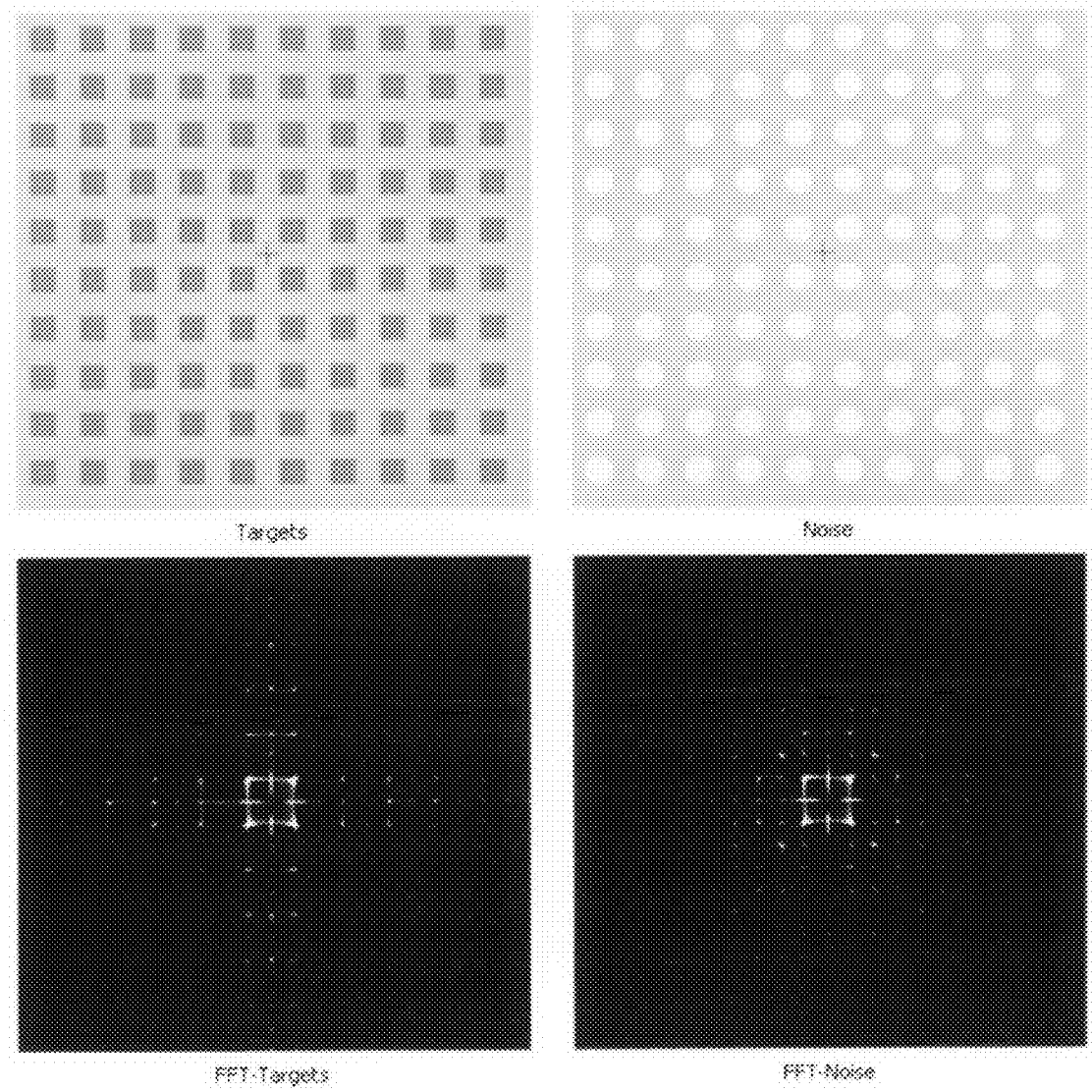
FIG. 1 shows two sample stimuli, a target dark stimulus, and noise bright stimulus, along with their corresponding frequency spectra (Fourier-transformed) below. The mean luminance of the two images (zero-spatial frequency within the Fourier domain) are identical, and the fundamental spatial frequencies are identical, while the power is spread out more to the diagonals for the noise stimuli. The area of the shapes is identical between the two images.

The invention is a neuropsychological test method. Its primary purpose is as a visual assessment of attentional mechanisms, able to distinguish different patterns of attentional performance and compare them with normative data. However, it also has utility in measuring critical flicker fusion, and a measure of fine motor speed.

The invention relies on a lookup table created with the assistance of a photometer to associate the monitor's gray levels (0-255 for 32-bit color, 0-65535 for 64-bit color) with photometric luminance. These luminance levels are computed at least once every three months, in order to ensure a high degree of accuracy in stimulus generation.

Using this data (and the subject's chromatic flicker fusion points for chromatic stimuli), the invention presents stimuli believed to preferentially elicit each individual visual pathway, particularly the magnocellular, parvocellular chromatic, koniocellular, and parvocellular achromatic. In order to assess the function of the glutamate-based non-linear contrast gain control system, additional high luminance-contrast stimuli are presented.

While configurable, the invention is intended for use on a high resolution, high color depth and high refresh rate display. The invention is capable of functioning in either a 32-bit or 64-bit color depth, and translating each gray level to an expected luminance based on the photometric calibration. The invention is intended to run at a high refresh rate, in order to reduce or eliminate external flicker and have a high degree of control in stimulus presentation. The invention has been tested at a refresh rate of 120 Hz.

Before the test begins, participants' isoluminant points are determined for red, green, yellow, and blue. This is achieved by displaying an isolated checkerboard against the same background used during the actual test. Using the up/down keys, the participants control the depth of modulation of each of the colors, while the frequency is set at 20 Hz. This frequency is configurable, however, in case the participant is unable to perceive modulation at that high a frequency. The monitor is set to the same resolution and refresh rate as is used during the test session.

Furthermore, critical flicker fusion is measured using a small external device consisting of several light emitting diodes (LEDs) and an amplifier, connected to the computer's sound card. The sound card emits a pure tone (either sine or square wave), which via the amplifier, drives the LEDs. The participant is asked to several times control the frequency of the sound in order to locate the point at which the perceived flickering appears or disappears. After ten trials (five until the modulation disappears, five until it appears), the average frequency is recorded. Based on current understanding of the visual system, this frequency will provide an additional understanding into the intactness of the participant's magnocellular function.

After measuring the participant's isoluminant and critical flicker fusion points, chosen physiological measurement devices are calibrated. If galvanic skin response is included, baseline measurements are collected at this point. Participants are additionally offered to spend a few minutes to get used to the test paradigm via a practice session.

Stimuli for the invention consist of a 10×10 isolated checkerboard pattern centered on the screen, either consisting of filled squares or filled circles (See FIG. 1). At the center of the image is a fixation crosshair intended to assist the participant to maintain visual focus, and to provide a target point for an eye tracker in order to determine the degree of visual drifting that occurs.

The stimuli are presented centered on the screen, against a background of a set luminance. The stimuli are calibrated so that each has identical height and width when displayed on the screen at the set resolution. In the event that the intended luminance of the squares is not equal to the luminance of a particular gray level, pixels of the luminance levels directly above and below that point are interspersed to create a stimulus with an average luminance nearly identical to the intended level. This same weighted averaging is used to produce the background at the intended luminance. This weighted averaging helps ensure that the invention functions well across multiple platforms and over time.

The luminance levels of the shapes and the mode of their presentation (spontaneous, gradual or pedestal) are based on the target visual pathway. Participants are instructed to respond to the square stimuli (targets) and not to the circle stimuli (noise). Depending on the mode of testing, participants respond either by pressing down on a lever and quickly releasing it, or by releasing a lever and quickly repressing it and holding it down until the next target.

When analyzed in the frequency (Fourier) domain, the target and noise stimuli have identical zero and fundamental spatial frequencies, although the power is more spread to the diagonals for the noise stimuli than for the target stimuli.

For the magnocellular pathway, the stimuli are presented with a spontaneous onset, at a low percentage above ($M_{ON}$) or below ($M_{OFF}$) the background gray luminance level. Currently, the invention has been tested with values 8% and 6%. For the parvocellular chromatic pathways, the stimuli are presented at isoluminance, as red ($PC_R$) or green ($PC_G$) stimuli against a gray background. For the koniocellular pathway, the stimuli are presented at isoluminance, as blue ($KN_B$) or yellow ($KN_R$) stimuli against a gray background. For the parvocellular achromatic pathway, the stimuli modulate around a high background contrast (pedestal), starting at background, ramping to a positive (PN) or negative (PF) contrast, and then modulating first downward ($PN/PF_{DN}$) or upward ($PN/PF_{UP}$). In order to assess the functioning of the NMDA-based non-linear contrast gain control system, stimuli are presented with a spontaneous onset at a high percentage (50%) above ($CG_{ON}$) and below ($CG_{OFF}$) the background luminance level. See FIG. 2 for further information on these stimulus types.

While taking this test, several physiological measurements are obtained every 0.25 seconds. Measures, as available, currently include galvanic skin response (GSR), heart rate, blood pressure, eye position (deviation from the fixation crosshair) and pupil dilation. The invention can, using dynamic link libraries (DLLs), receive configurable data either in real time or by import after a test's completion.

The apriori probability of a stimuli being a target will vary across the test between 25%, 50%, and 75%. See FIG. 3 for a sample of a test pattern designed to balance stimulus types across the testing session. While configurable, the stimulus presentation duration defaults to 250 ms, and the time between the offset of one stimulus and onset of the next defaults to 1, 2, and 4 seconds. An alternate configuration supports two adjacent stimulus presentations of a set presentation time (e.g., stimulus presentation for 100 ms, blank for 50 ms, present again for 100 ms).

After each stimulus is presented on the screen, a response from the participant before the presentation of the next stimulus is noted. If a response occurs and the stimulus was a target, it is considered a hit. If a response occurs and the stimulus is noise, it is considered a false alarm. A non-response to noise is considered a correct rejection, and non-response to a target is considered a miss. In the event of a response to a stimulus, the time between the initial onset of the stimulus and the response is recorded (reaction time to hits, reaction time to false positives). When the participant stops responding (by either releasing or repressing the lever depending on the instructions), the differential between the beginning and end of the response is computed (reset time to hits, reset time to false positives).

If responding is measured in a continuous fashion, threshold computations are made at liberal, average, or conservative levels of what is considered a response based on the range of the participant's responding. Computations of means, standard deviations, and accelerations are presented for each interpretation.

Upon completion of the task, the invention computes the following variables based on the test data:
1. Raw Response Variables
   a. Hit proportion (number of hits/number of targets)
   b. False alarm proportion (number of false alarms/number of noise)
   c. Correct Rejection proportion (number of correct rejections/number of noise)
   d. Miss proportion (number of misses//number of targets)
   e. Percent correct ((number of hits+number of correct rejections)/number of stimuli)
   f. Standard error of percent correct
2. Timing-Based Variables
   a. Mean and standard deviation: reaction time to hits, reaction time to false alarms
   b. Mean and standard deviation time: reset time to hits, reset time to false alarms
3. Signal Detection Theory (CT) Variables (Green & Swets, 1966)
   a. Sensitivity (d') and standard error
   b. Criterion location (c) and standard error
   c. Relative criterion location (c')
   d. Response likelihood ratio ($\beta_G$)
4. Choice Theory (CT) Variables (Luce, 1959)
   a. Sensitivity (.alpha.)
   b. Transformed sensitivity ($\ln(\alpha)$)
   c. Bias (b)
   d. Transformed bias/criterion location ($\ln(b)$)
   e. Relative criterion location (b')
   f. Response likelihood ratio ($\beta_L$)
5. Non-parametric detection theory (NPDT) variables (Macmillan, N. A., Creelman, C. D. (1991). Detection Theory: A User's Guide. New York: Cambridge University Press)
   a. Sensitivity (q)
   b. Criterion location (k)
   c. Relative criterion location (k')
   d. Sensitivity (A')
   e. Transformed sensitivity (A")
   f. Bias (B")
6. Physiological variables (as available)—each value's mean, mode, median, Minimum and Maximum are Correlated with Raw, Timing, SDT, CT and NPDT Variables.
   a. Galvanic Skin Response
   b. Eye tracking location variables (Deviation of vertical and horizontal offset from the fixation crosshair)
   c. Pupil dilation
   d. Eye tracking saccade counts
   e. Eye tracking loss (eye blink) counts
   f. Blood pressure
   g. Heart rate
   h. Any other physiological measure that can be reported to the invention through an external device (continuous or discrete variables), or computed from that data.

Each of these variables is computed for each stimulus type believed to preferentially elicit a particular visual pathway (magnocellular on, magnocellular off, parvocellular chromatic red, parvocellular chromatic green, koniocellular blue, koniocellular red, parvocellular achromatic on-up, parvocellular achromatic on-down, parvocellular achromatic off-up, parvocellular achromatic off-down, contrast gain on, contrast gain off). Computations are also performed for the aggregate magnocellular, parvocellular chromatic, koniocellular and contrast gain stimuli, as well as for all ON and all OFF stimuli. Differential measures are also computed between each ON and OFF stimuli, between the parvocellular achromatic UP and parvocellular achromatic DOWN stimuli, and between each type of stimuli.

While the foregoing is illustrative of a preferred embodiment of the invention, other embodiments and modifications and improvements are intended to come within the scope of the invention and of the appended claims.

The invention claimed is:
1. A non-invasive neuropsychological test system to provide a variable contrast continuous visual performance test of a subject, said system comprising:
   a. a computer system comprising a monitor having a color depth, a memory, a lever, a photometer, and an instrument for measuring critical flicker fusion having several light emitting diodes;
   b. establishing a luminance lookup table to associate gray levels displayed by the monitor with photometric luminance levels with said photometer according to said color depth, translating each gray level to an expected luminance level, and recording the luminance lookup table in the memory;
   c. measuring a critical flicker fusion of the subject with the instrument for measuring critical flicker fusion, comprising presenting the subject with a signal having a flickering appearance in said light emitting diodes according to a frequency, allowing the subject to control the frequency to a point at which the flickering appear- ance disappears or the critical flicker fusion, and recording the critical flicker fusion in said memory;
d. measuring isoluminant points of the subject for colors red, green, yellow and blue, comprising presenting the subject with an isolated checkerboard of each of said colors displayed on the monitor against a test gray background and allowing the subject to select isoluminant points of each of said colors relative to the test gray background, and recording the isoluminant points of the subject for colors red, green, yellow and blue in said memory;
e. measuring a response of the subject to visual stimuli, comprising presenting the subject with the visual stimuli based on a pattern of visual stimuli according to the luminance lookup table and the isoluminant points of said subject, said pattern comprising a continuous series of stimuli having an a priori probability level of being a target stimulus, said apriori level being 25%, 50% and 75%, allowing the subject to respond to said stimulus when said target stimulus appears on the monitor by manipulating the lever, and recording response of the subject to said visual stimulus in the memory; and
f. determining the visual function and the visual attention of the subject based on the response of the subject to the visual stimuli;
wherein the continuous series of stimuli comprises a 10×10 isolated checkerboard pattern centered on the monitor, being a target stimulus of filled squares, or a noise stimulus of filled circles, against the test gray background, said continuous series of stimuli selected from the group consisting of Magnocellular On ($M_{ON}$), Magnocellular On ($M_{OFF}$), Parvocellular Chromatic Green ($PC_G$), Parvocellular Chromatic Red ($PC_R$), Koniocellular Blue ($KN_B$), Koniocellular Yellow ($KN_Y$), Parvocellular Achromatic ON-Up ($PN_{UP}$), Parvocellular Achromatic On-Down ($PN_{DN}$), Parvocellular Achromatic OFF-Up ($PF_{UP}$), Parvocellular Achromatic OFF-Down ($PF_{DN}$), Non-linear Contrast Gain Control On ($CG_{DN}$), Non-linear Contrast Gain Control Off ($CG_{OFF}$), said series of stimuli being displayed according to the presentation pattern in FIG. 3, wherein the noise stimulus being shown as underlined, each stimulus being displayed at a duration time and a variable time between one stimulus and the onset of a next stimulus.

2. The non-invasive neuropsychological test system of claim 1, wherein the duration time is 250 ms and the variable time between one stimulus and the onset of a next stimulus is selected from the group consisting of 1, 2, and 4 seconds.

3. The non-invasive neuropsychological test system of claim 1, wherein the duration time is two adjacent stimuli consisting of 100 ms, blank for 50 ms, and present again for 100 ms.

4. The non-invasive neuropsychological test system of claim 1, wherein the lever is a device selected from the group consisting of a button, a custom switch, and a mouse button.

5. The non-invasive neuropsychological test system of claim 1, wherein the subject responds to each stimulus by pressing down on the lever and quickly releasing the lever, or by holding the lever down.

6. The non-invasive neuropsychological test system of claim 1, wherein the instrument for measuring critical flicker fusion further comprises and amplifier connected to the computer system wherein a sound card emits a pure tone which drives the light emitting diodes.

7. The non-invasive neuropsychological test system of claim 1, wherein the color depth of the monitor is a 32-bit color or 64-bit color.

8. The non-invasive neuropsychological test system of claim 1, further comprising measuring and recording galvanic skin response during the variable contrast continuous visual performance test.

9. The non-invasive neuropsychological test system of claim 1, further comprising electronically measuring and recording additional biophysical measurements during the variable contrast continuous visual performance test.

10. The non-invasive neuropsychological test system of claim 9, wherein the additional biophysical measurements are selected from the group consisting of heart rate, blood pressure, eye movement, and pupil dilation.

11. The non-invasive neuropsychological test system of claim 1, wherein measuring the response of the subject to a visual stimulus in claim 1, step (e) includes:
a. measuring a degree to which the lever is pressed in a variable response,
b. measuring whether the lever is pressed in a binary response,
c. measuring release of the lever if pressed in a button up response,
d. measuring pressing the lever if released in a button down response, and
e. measuring pressing the lever back down in a response conclusion.

12. The non-invasive neuropsychological test system of claim 1, wherein the Parvocellular Achromatic On-UP has a contrast level being modulated +48%, plus or minus 16% initially upward.

13. The non-invasive neuropsychological test system of claim 1, wherein the Parvocellular Achromatic On-Down has a contrast level being modulated +48%, plus or minus 16% initially downward.

14. The non-invasive neuropsychological test system of claim 1, wherein the Parvocellular Achromatic Off-UP has a contrast level being modulated −48%, plus or minus 16% initially upward.

15. The non-invasive neuropsychological test system of claim 1, wherein the Parvocellular Achromatic Off-Down has a contrast level being modulated −48%, plus or minus 16% initially downward.

* * * * *